United States Patent
Bublitz et al.

(10) Patent No.: US 8,596,786 B2
(45) Date of Patent: Dec. 3, 2013

(54) ARRANGEMENTS AND METHOD FOR MEASURING AN EYE MOVEMENT, PARTICULARLY A MOVEMENT OF THE FUNDUS OF THE EYE

(75) Inventors: Daniel Bublitz, Jena (DE); Stefan Richter, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 182 days.

(21) Appl. No.: 13/121,557

(22) PCT Filed: Sep. 22, 2009

(86) PCT No.: PCT/EP2009/006816
§ 371 (c)(1),
(2), (4) Date: Mar. 29, 2011

(87) PCT Pub. No.: WO2010/037485
PCT Pub. Date: Apr. 8, 2010

(65) Prior Publication Data
US 2011/0176110 A1 Jul. 21, 2011

(30) Foreign Application Priority Data

Sep. 30, 2008 (DE) .......................... 10 2008 049 846
Sep. 30, 2008 (DE) .......................... 10 2008 049 881

(51) Int. Cl.
*A61B 3/14* (2006.01)
(52) U.S. Cl.
USPC ............................ 351/209; 351/206; 351/210
(58) Field of Classification Search
USPC .......................................... 359/206, 209, 210
See application file for complete search history.

(56) References Cited

U.S. PATENT DOCUMENTS

| 4,952,050 | A | 8/1990 | Aizu et al. |
|---|---|---|---|
| 4,979,818 | A | 12/1990 | Kobayashi |
| 5,090,799 | A | 2/1992 | Makino et al. |
| 5,615,683 | A | 4/1997 | Toge et al. |
| 5,644,642 | A | 7/1997 | Kirschbaum |
| 5,786,804 | A | 7/1998 | Gordon |
| 6,726,325 | B2 | 4/2004 | Xie et al. |
| 7,161,682 | B2 | 1/2007 | Xie et al. |
| 7,878,910 | B2* | 2/2011 | Wells .............................. 463/46 |
| RE42,998 | E * | 12/2011 | Teiwes et al. ................. 382/117 |
| 2005/0024586 | A1 | 2/2005 | Teiwes et al. |
| 2006/0228011 | A1 | 10/2006 | Everett et al. |
| 2010/0303294 | A1* | 12/2010 | Zschau ........................ 382/103 |

FOREIGN PATENT DOCUMENTS

| DE | 689 11 975 T2 | 5/1994 |
|---|---|---|
| DE | 690 20 410 T2 | 12/1995 |
| EP | 0337745 B1 | 10/1989 |
| EP | 0 392 742 A1 | 10/1990 |

(Continued)

*Primary Examiner* — Jordan Schwartz
(74) *Attorney, Agent, or Firm* — Patterson Thuente Pedersen, P.A.

(57) ABSTRACT

In addition to a first detector for capturing a potential movement field of the eye in overview images, a second detector is used to capture a particular section of the eye in sectional images. From a displacement between two overview images and an intermediate displacement between two sectional images taken between said overview images, the eye movement is determined by linking said displacements. The sections are preferably illuminated by coherent light such that interfering light diffused on the eye produces a patch pattern. Alternatively, the sclera of the eye is illuminated with coherent light such that light diffused on the sclera produces a patch pattern, of which a particular part is captured using a spatially resolving detector in sectional images, on the basis of which an intermediate displacement is determined.

13 Claims, 5 Drawing Sheets

(56) References Cited

FOREIGN PATENT DOCUMENTS

| | | | |
|---|---|---|---|
| EP | 0392742 B1 | 10/1990 | |
| JP | 60174905 A | 9/1985 | |
| WO | WO 01/89438 A2 | 11/2001 | |
| WO | WO 2007/127291 A2 | 11/2007 | |
| WO | WO 2008/077854 A1 | 7/2008 | |

* cited by examiner

ARRANGEMENTS AND METHOD FOR MEASURING AN EYE MOVEMENT, PARTICULARLY A MOVEMENT OF THE FUNDUS OF THE EYE

PRIORITY CLAIM

The present application is a National Phase entry of PCT Application No. PCT/EP2009/006816, filed Sep. 22, 2009, which claims priority from German Application Number 102008049881.5, filed Sep. 30, 2008, and German Application Number 102008049846.7, filed Sep. 30, 2008, the disclosures of which are hereby incorporated by reference herein in their entirety.

FIELD OF THE INVENTION

The invention relates to arrangements and methods for the (fast) measurement of a movement of a human eye, particularly an eyeground (fundus), by means of a two-dimensional spatially resolving detector for repeated imaging of a potential motion field of the eye in overview images.

BACKGROUND

For quite some time, motion tracking arrangements for the measurement and tracking of the eye movement (eye trackers) have been utilized in ophthalmology and other fields of application for, among others, the purpose of research, diagnosis, and therapy. For example, during a treatment of the eye (cornea, retina) by means of a surgical laser, it has to be ensured that the input of light energy takes place de facto in those areas in the eye, which are to be planned in advance of the treatment, in order to avoid damage to the eye. This is achieved either through deactivation of the laser the moment an eye movement is detected, or through adjusting of the laser beam by means of illumination optics in accordance with the measured eye movement. Further applications of the eye movement measurement are the controls of machines, e.g., computers or motor vehicles.

According to prior art, the pupil of the eye is in most cases imaged repeatedly in succession by means of a high-speed video camera at a high image refresh rate, e.g., in accordance with WO 01/89438 A2. By means of specific image evaluation algorithms, e.g., through edge detection, the relatively sharp boundary between the black eye pupil and the lighter iris can be identified in the recorded images. In principle, the eye movement can be determined from shifts of said boundary and/or the pupil center in sequential images. In order to detect eye movements with smaller amplitude, the images must be taken with high optical resolution and sharpness. In order to also detect eye movements with large amplitude, the potential motion field of the pupil must be included in the images as extensively as possible. The combination of both requirements necessitates the detection of images with a high number of pixels.

However, the readout of such large images from the camera sensor and the subsequent analysis of, at least, partial image areas take a relatively long time due to the amount of data, resulting only in low, effective image refresh rates, i.e., rates for the recording, including the subsequent analysis, of no more than a few 100 Hz. However, the human eye can perform so-called saccade movements at a speed of approximately up to 600° per second. In order to achieve great accuracy of the motion measurement at such speeds, a significantly higher effective image refresh rate must be achieved. For the tracking-adjustment of a therapy laser during a femtosecond Lasik surgery, e.g., an effective image refresh rate of at least 1 kHz would be required. However, according to prior art, this can only be achieved through limiting of the spatial resolution or the observed maximum motion field.

The measurement of the movement of the eye fundus, particularly during a treatment of the retina, e.g., a laser coagulation, poses the additional problem that the necessary illumination must only lie within the infrared (IR) wavelength range in order to avoid a glare and therefore a blink reflex, even though the eye fundus is poor in contrast in the IR range. For example, IR illumination is used with non-mydriatic fundus cameras during alignment and adjustment. Visual light is only briefly introduced during a color image acquisition, which typically leads to a blink only at the end of the exposure time. In order to determine a movement of the eye fundus, particularly for the tracking-adjustment of a laser, with sufficient accuracy, the recorded IR images must be analyzed in significantly larger partial image areas than is required for edge detection on the pupil. As a result, the effective image refresh rate is further reduced. Alternatively, the movement of the eye fundus can be determined from a positional change of larger blood vessels. However, since the eye fundus only exhibits a few larger blood vessels, only a small portion of the eye fundus can be utilized for this type of analysis, hence measurements can only be taken in a limited motion field.

In addition to the motion measurement with the help of video recordings, the movements, particularly of the eye fundus, can be measured with scanning laser motion tracking arrangements. Said systems, known, e.g., from US 2006/228011, U.S. Pat. Nos. 6,726,325, and 5,644,642, confocally scan a preferably greatly structured portion of the eye fundus with a laser beam. Thereby, the scan can be performed circularly around a thicker vein branch or around the papilla of the eye. Said systems are advantageous because the sensors can be adjusted to the geometry of the specific eye. As a result, they only have to scan a few points of the eye fundus in order to detect movements with great accuracy, therefore allowing for a quick and uncomplicated evaluation of the image content. However, they are disadvantageous because an elaborate laser scanner is required.

SUMMARY OF THE INVENTION

The invention is based on the task of improving an arrangement and a method of the initially described type in such a way that a higher effective image refresh rate than in prior art is possible with great spatial measurement accuracy and minimal expenditure.

According to the invention, it has been realized that during the measurement of an eye movement, the effective image refresh rate can be significantly increased through a combination of a slow, large-format motion measurement arrangement with a fast, small-format motion measurement arrangement.

Therefore, according to the invention, in addition to the first two-dimensional spatially resolving detector for the repeated imaging of a potential motion field of the eye in overview images, which each contain a first number of image elements, with a first image refresh rate, a second two-dimensional spatially resolving detector is positioned for the repeated imaging of a respective eye segment in sectional images, which each contain a second number of image elements, with a second image refresh rate, which is higher than the first image refresh rate; a data processor is arranged for the determination of an intermediate shift by means of two mediately or immediately consecutive overview images, and an intermediate shift by means of two sectional images taken between said mediately or immediately consecutive overview images, as well as for the determination of a movement of the eye through the interlinking of said shifts. A shift in accordance with the invention is, e.g., a two-dimensional vector. Such a vector can, e.g., describe an offset between the images. Interlinking in accordance with the invention refers to the series connection of the two shifts, e.g., through vectorial addition. For the determination of the movement, the determined two-dimensional shift is expediently converted to a two-dimensional rotation. After the determination of the movement, it is expediently read out for processing.

Advantageously, the second number of image elements is smaller, particularly, significantly smaller, than the first number of image elements in order to reach the higher second image refresh rate. In addition, due to the lower number of pixels of the sectional images, their analysis for the determination of the shift can be performed quicker.

The increase of the effective image refresh rate for the measurement of the eye movement is effected through said combination of characteristics by interpolating the measurement of the eye movement, to put it simply, in the time between the overview images taken with the lower image refresh rate by means of the sectional images taken with the higher image refresh rate. The shifts, extracted from the high-resolution overview images, which encompass the entire potential motion field, are used for recalibration in order to avoid an error propagation of the shifts extracted from the sectional images.

Thereby, the recalibration is preferably achieved through comparison of the most recently taken overview image with invariably the same (constant) earliest overview image, preferably taken at the beginning of the procedure. Advantageously, a quasi-absolute initial position of the eye in said earliest overview image can be determined through manual or automatic (e.g., by means of image processing algorithms) comparison with an earlier treatment planning image. The shifts from the smaller sectional images can be determined with great speed, resulting in a high effective image refresh rate. With the help of said high effective image refresh rate, a therapy laser can be tracking-adjusted with great spatial-temporal accuracy during the positioning on planned light energy inputs.

Preferably, the shifts are determined through comparison of at least one respective part of the image content of the respective two images, e.g., by means of cross-correlation. In this manner, two-dimensional shifts can be determined with little effort. The utilization of the correlation technique is described in U.S. Pat. No. 5,786,804, the content of disclosure of which is hereby incorporated herein in its entirety. For example, an optimized comparison can be effected through primarily examining a direction of motion which is known from a previous shift. Only when the examination proves that the movement did not continue in said direction, the remaining possible directions are examined secondarily.

In a particularly preferred embodiment, a first light source for the illumination of the potential motion field of the eye with incoherent light, and a second light source for the illumination of the respective segment of the eye with coherent light are provided in such a way that a speckle pattern forms in the respective segment through interfering coherent light, scattered at the eye, while the second detector is designed for imaging of at least one part of the speckle pattern in the respective sectional image. The speckle pattern is formed on the eye through the scatter at a microstructure in the volume of the eye tissue, e.g., in the sclera or the retina.

Through the formation and the imaging of the high-contrast speckle pattern in the sectional images, a shift, and therefore the eye movement, can be determined even in a low-contrast area of the eye since the speckle pattern moves to the same extent as the eye movement. The shift of the speckle pattern can, e.g., be determined through an image comparison by means of cross-correlation. The correlation of speckle patterns is described, e.g., in JP 60174905.

Thereby, the second detector preferably exhibits optics for the magnified imaging of the speckle pattern on the second detector in such a way that individual speckles of the speckle pattern exhibit a size which approximately corresponds to or is larger than a size of image elements of the second detector. As a result, the shift of the speckle pattern between the sectional images can be determined with great accuracy.

For the measurement of a movement of a fundus of the eye, the first light source for the illumination of the eye fundus is preferably designed for infrared light; the first detector is designed for imaging at least a portion of the eye fundus as a potential motion field of the eye; and the second light source is designed for the illumination of a respective segment of the eye fundus with infrared light. Through the use of infrared light, a glare and therefore a blink reflex are avoided during the measurement of the movement of the eye fundus.

Preferably, the second light source is designed for a plane illumination angle between 1° and 10°. As a result, an excessive energy density as occurs, e.g., with a confocal spot illumination, is avoided.

Interfering light reflexes on the eye, particularly on the anterior of the cornea, can be avoided or at least diminished through the essentially spot-shaped design of the second light source in the plane of the eye pupil. For example, this can be realized through an essentially circular design of a second light source plane, which is conjugated to the eye pupil.

Preferably, the second light source is designed for focusing of the coherent light in a plane which is conjugated to a pupil of the eye. Due to the conjugated positioning, the arrangement, according to the invention, can be integrated in a conventional fundus camera with little effort.

Advantageously, the imaging and illumination beam paths are designed in such a way that an average angle of incidence of the coherent light of the second light source onto the eye essentially corresponds to an observation direction of the second detector. This can be realized, e.g., through the coupling of the imaging and illumination beam paths by use of one or several beam splitters/combiners. Particularly, this can be achieved with mirrors which reflect a geometric part of the respective beam path and leave another geometric part untouched, e.g., ring mirrors.

The arrangement, according to the invention, can be realized with little effort by using a detector of a laser mouse as the second detector. Such detectors are available at low cost due to large quantities and standard electronics. Typically, evaluation electronics for generating correlations between sequential sectional images are integrated in such detectors.

Preferably, the second detector is positioned in a plane which is optically conjugated to the respective segment. In the case of the measurement of the movement of the eye fundus, the respective segment lies in the eye fundus, so that the second detector is conjugated to the eye fundus. Due to the conjugated position, the arrangement, according to the invention, can be integrated with little effort in a conventional fundus camera.

The arrangement, according to the invention, can be utilized particularly advantageously in a fundus camera or in an ophthalmological laser system as motion tracking arrangement for a therapy laser and/or for the deactivation of the therapy laser when a (e.g., too extensive) eye movement is detected. As a result, surgical procedures, laser coagulations, or photodynamic therapies (PDT) in the eye fundus can be performed with great accuracy.

Preferably, the fundus camera and/or the laser system exhibits a non-reflective front objective for illumination and detection, or with regard to the arrangement, according to the invention, an off-axis illumination and detection. This way, interfering light reflexes at the front objective can be avoided.

According to the invention, it has further been realized that an eye movement can also be determined with an accuracy sufficient for some applications solely by use of a single fast detector, whereby a light source illuminates a sclera of the eye with coherent light during the repeated taking of sectional images by means of the two-dimensional spatially resolving detector in such a way that a speckle pattern is formed through interfering light, which is scattered on the sclera, whereby the detector must be designed for the imaging of at least one part of the speckle pattern into the sectional images. A shift in accordance with the invention is, e.g., a two-dimensional vector. Such a vector can, e.g., describe an offset between the images. Then, a movement of the eye can be determined, e.g., with a data processor, by means of an intermediate shift of the speckle pattern, whereby the shift is determined by use of two sectional images. As a result, an elaborate evaluation of the image content, e.g., through an edge detection, can be foregone since at a high image refresh rate, only a few pixels need to be evaluated in order to determine the shift of the speckle pattern. Preferably, the data processor determines the shift through comparison of the image content of the respective sectional images, e.g., by means of correlation. After the determination of the movement, it is expediently read out for processing.

In one embodiment, the detector exhibits optics for the magnified imaging of the speckle pattern on the detector in such a way that individual speckles of the speckle pattern exhibit a size which approximately corresponds to or is larger than a size of image elements of the detector. As a result, the shift of the speckle pattern between the sectional images can be determined with great accuracy.

In one embodiment, the coherent light source is designed for a plane illumination of an area between 10 µm×10 µm and 1 mm×1 mm. As a result, an excessive energy density as occurs, e.g., with a confocal spot illumination, is avoided.

In another embodiment of the invention, the imaging and illumination beam paths are designed in such a way that an average angle of incidence of the coherent light onto the eye essentially corresponds to an observation direction of the detector. This can be realized, e.g., through coupling of the imaging and illumination beam paths by means of one or several beam splitters/combiners.

The arrangement, according to the invention, can be realized with little effort, whereby a detector of a laser mouse is used as the detector. Such detectors are available at low cost due to large quantities and standard electronics. Typically, evaluation electronics for generating correlations between sequential sectional images are integrated in such detectors.

The arrangement, according to the invention, can be utilized particularly advantageously in a fundus camera or in an ophthalmological laser system as a motion tracking arrangement for a therapy laser and/or for the deactivation of the therapy laser when a (e.g., too extensive) eye movement is detected. As a result, surgical procedures can be performed with great accuracy.

In one aspect, the fundus camera and/or the laser system exhibits a non-reflective front objective for illumination and detection, or with regard to the arrangement according to the invention, an off-axis illumination and detection. This way, interfering light reflexes at the front objective can be avoided.

The invention includes embodiments, in which, e.g., by the data processor, more than two recorded sectional images are assembled mosaic-like to an overview image by means of the respective determined shift, wherein the shift of the speckle pattern for the respective most recently taken sectional image is determined by comparison of the image content of said sectional image with the image content of the overview image. As a result, the error propagation can be decreased within the course of the shifting during several consecutive recordings.

The invention also comprises computer programs and control units for the execution of the method, according to the invention, particularly data carriers, which contain such computer programs, as well as ophthalmological devices, which comprise an arrangement, according to the invention.

BRIEF DESCRIPTION OF THE DRAWINGS

In the following, the invention shall be further explained by means of embodiment examples.

It is shown in.

DETAILED DESCRIPTION

In all drawings, all corresponding parts bear the same legend.

If a scattering surface, such as paper or a wall, is illuminated with a laser or any other spatially and temporally coherent light source, the light that is backscattered from the surface can interfere in the space, whereby a typical pattern of grainy structures or speckles occurs, which, in accordance with the invention, is termed speckle pattern. A distinction is made between subjective and objective speckles. Subjective speckles occur when the scattering surface is imaged with optics on the camera sensor. The subjective speckles exhibit exactly the same size as the optical resolution of the imaging system. The subsequently registered speckle pattern moves with the shifts of the scattering surface, thus allowing for a quantitative determination of the shift. Objective speckles occur when the camera sensor is positioned without optics in the light backscattered from the sample. Objective speckles react to tilts of the sample surface. The size of the objective speckles is calculated from the wavelength of the radiation, the diameter of the illuminated sample surface, and the distance between sample surface and camera sensor. Among others, the following values, particularly on an eye, can be measured with the speckle correlation technique:

a) Measurement of the distance of a scattering surface from a contact surface, e.g., for autofocusing. A laser wave with a certain aperture is focused on the sample surface. The light wave backscattered from the surface of the sample is registered with a camera sensor without optics. The average size of the objective speckles is determined by determining the full width at half maximum of the autocorrelation function of the camera images. Said full width at half maximum, at fixed wavelength and distance of the camera from the scattering surface, is directly proportional to the diameter of the illuminated surface. Since, through focusing of the illumination wave, the diameter of the illuminated surface depends on the distance of the scattering surface from the focal plane of the illumination wave, a distance sensor can be realized in this fashion.

b) Measurement of the shift of a scattering surface: A laser wave is imaged onto the sample surface to be measured.

The light backscattered from the sample is imaged onto a camera sensor with the help of an optical system. Due to the image artifacts and the diffraction, a certain part of the sample is always imaged through the optics on a point of the camera surface. Thereby, the object distribution is folded with the point-spread function (PSF) of the optical system and thereby results in the detected image. Due to the coherence of the laser wave, the light, which impinges on a pixel of the camera sensor, can interfere and, as a result, produces the speckle pattern with speckles, the average size of which equals the full width at half maximum of the diffraction-limited PSF. During lateral shifts, said speckle pattern moves along with the scattering surface. Through the forming of the cross correlation between two consecutively taken images of the speckle pattern, size and direction of the relative shift between the two images can be determined. The method is robust since the correlations in the backscattered light field are measured instead of the structures of the sample. The structuring of the image occurs through the coherent properties of the illumination wave in connection with the statistical phase variance through the scatter on the surface. For the cross correlation, small, low-resolution camera sensors with a few hundred pixels can be utilized, which allows for a very high measuring speed in the kilohertz range. Through a combination of the measurement of the objective and subjective speckles, a three-dimensional displacement vector can be determined. The positional and angular changes of a general surface can be determined with several sensors, and thus the movements of a human eye can be recorded in all degrees of freedom. A similar method for the two-dimensional determination of shifts is used with optical computer mice, whereby the correlations are measured in the light backscattered from the table.

In order to realize a motion measurement, which is optimized with regard to speed and accuracy, at first the motion degrees of freedom of the system have to be determined. Said motion degrees of freedom can depend greatly on the application to be realized. In principle, the eye together with the head can shift in all three spatial directions and/or tilt around three angles. In addition, the eye can rotate in the eye socket around two angles (horizontally, vertically). Therefore, the measurement of all movements of the eye would require the determination of three shifts and three angular changes.

However, for some ophthalmological applications, the movement of the eye is measured and compensated only for approximately 1 second. In such a case, only the fast eye movements must be measured instead of the head movements. In that case, two degrees of freedom (horizontal and vertical rotation angle), which can be measured with a sensor, will suffice. In addition, an autofocus sensor, which measures the distance of the cornea to the treatment device, would be required in case of refractive therapy of the cornea.

Figure 1:
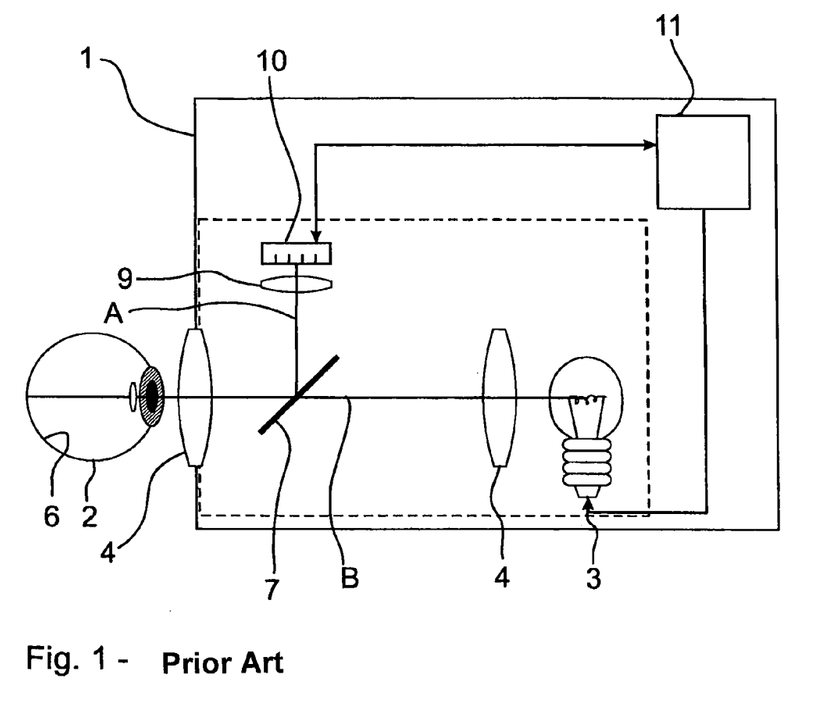
FIG. 1 depicts a conventional fundus camera.

At first, the measurement of the movement of the eye fundus in a fundus camera shall be described. For said purpose, FIG. 1 shows a conventional fundus camera 1. In the illumination beam path B it exhibits a light source 3 with optical elements 4 for the focused illumination of the fundus 6 of the eye 2. The imaging beam path A is reflected in the illumination beam path B via a beam splitter 7 and contains detection optics 9 for imaging the eye fundus 6 onto the spatially resolving detector 10. The fundus camera 1 is operated by a control unit 14, which is connected to the detector 13 as well as to the light source 3.

Figure 2:
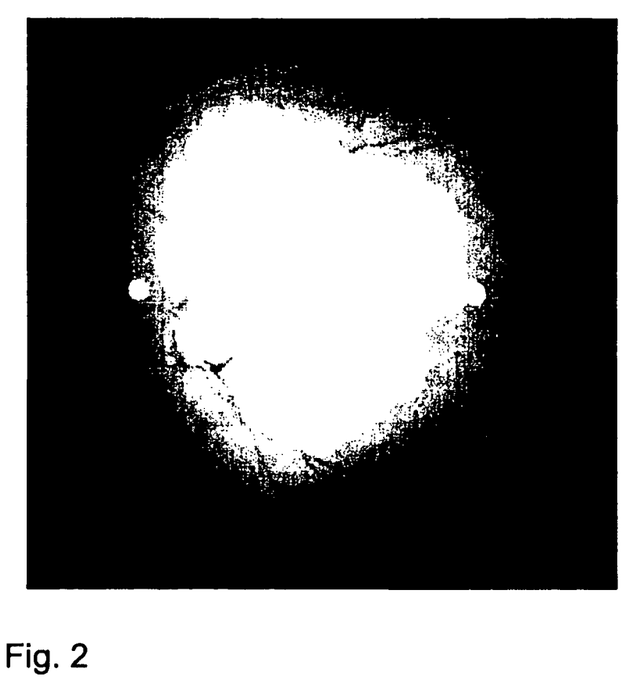
FIG. 2 depicts an infrared fundus image of high quality.

FIG. 2 shows an infrared fundus image of high quality. However, the contrast is still low, and a shift between two consecutive images, e.g., through correlation can only be determined with great effort (correlation of large image regions) and therefore slowly.

Figure 3:
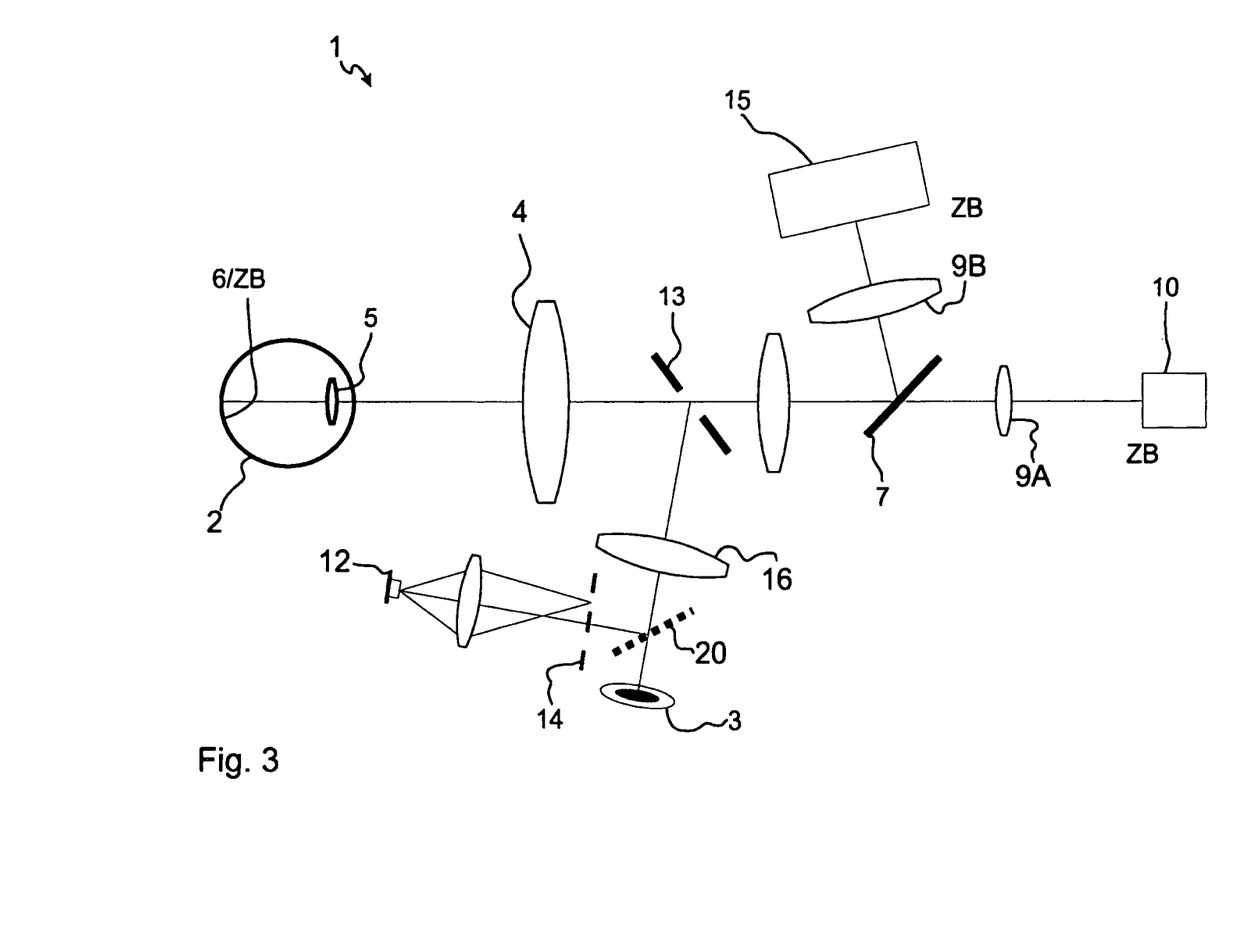
FIG. 3 is a schematic representation of a fundus camera with fast and slow motion measurement arrangement.

FIG. 3 schematically depicts a fundus camera 1, improved in accordance with the invention, with a fast and a slow motion measurement arrangement. The slow motion measurement arrangement comprises a first, incoherent IR light source 3 and a first IR detector 10, including detection optics 9A. The fast motion measurement arrangement comprises a second, coherent IR light source 12 for generating a speckle pattern through interference, and a second IR detector 15, including detection optics 9B for imaging of the speckle pattern. Both detectors 10, 15 are connected to a data processor (not depicted), which, by means of the first detector 10, continuously records overview images of the entire potential motion field of the eye fundus 6, and, by means of the second detector 15, records sectional images of the eye fundus 6.

The slow motion measurement arrangement has the advantage of allowing very reliably the shift of the eye fundus in quasi-absolute coordinates and therefore the reference to a previous fundus image. This makes preliminary planning of the treatment/diagnosis possible. Furthermore, with the help of the slow motion measurement arrangement with its relatively large image field, relatively large fundus displacements can be detected. The fast motion measurement arrangement is advantageous due to a very short latency period, high speed, and great reliability of the motion measurement, even if blurred and sparsely structured fundus areas are measured. However, its disadvantage is such that only relative shifts are measurable, making a treatment planning solely on this basis impossible. In addition, the calculation errors accumulate due to the paired comparison of consecutive images and can therefore, through error propagation, result in graver errors in the coordinate calculation of the entire shift.

For said reason, the shift of the eye fundus with regard to a previous image is performed at first with the slow motion measurement arrangement for the planning of the treatment. Then the movement of the eye fundus is continuously detected with the fast motion measurement arrangement. For example, an overview image is taken and evaluated twice per second with the slow motion measurement arrangement, whereby it is compared to the previous planning image. The movement determined therefrom is used to recalibrate the coordinate system of the fast motion measurement arrangement through interlinking of the determined shifts.

Operating principle of the slow motion measurement arrangement:

The entire eye fundus 6 is illuminated with a first IR light source 3, e.g., an IR-LED or a white-light lamp with spectral filter. The light backscattered from the eye fundus 6 is imaged on a spatially resolving detector 10, for example, a CMOS or CCD camera.

Overview images with an image refresh rate between 1 Hz and 30 Hz (images per second) are taken and displayed on a computer monitor (FIG. 2). The hardware for said slow part of the combined motion measurement arrangement is already technically available in all non-mydriatic fundus cameras as IR monitor or IR adjustment aid. From the overview fundus images thus recorded, a square image field with $2^n \times 2^n$ pixels is cut out, which contains as many specific, structured image details as possible. All overview images are cross-correlated against the first overview image and thus the shift of each of the overview images in comparison with the first overview image determined. The first overview image can be the first image of a series of overview images; then the shift of each additional overview image relative to the first overview image is known. In one embodiment variation, a color image and a corresponding IR image of the eye fundus 6 are taken with a standard fundus camera. With the help of said images, the physician can plan the therapy/diagnosis to be performed, e.g., a laser coagulation of areas of the eye fundus 6. At the beginning of the therapy/diagnosis, a first IR overview image of the eye fundus is recorded and correlated against the IR image of the therapy planning image in order to determine the initial position of the eye fundus 6. Then the subsequent overview images are always correlated against the first overview image or against the IR image of the therapy planning image. This way, e.g., previously planned points of the eye fundus can be approached and treated with a laser coagulator since the movement of the fundus 6 is measured with regard to the treatment planning. The image field for the correlation is selected at such a size that the maximum amplitude of eye movements, which occur in the specific observation case (e.g., supported by an inner fixation), i.e., the potential motion field of the eye fundus 6, is smaller than the size of the image field. A certain minimum size, which depends on the optical quality of the overview images, must not be undercut in order to guarantee a reliable detection of the eye fundus movement (which results in a preferred n=6 . . . 9).

The great advantage of the described method lies in the fact that it is technically provided for in every non-mydriatic fundus camera and can therefore be realized cost-effectively.

However, since the method provides for the use of standard monochrome cameras, as utilized in a non-mydriatic fundus camera, a typical readout time of at least 50 ms must be expected. The computation of the cross-correlations should preferably take place in a standard computer contained in the fundus camera and therefore requires approximately 500 ms, depending on the size of the image field to be correlated. As a result, the method with 550 ms is much slower than other motion measurement or motion tracking arrangements, which are part of prior art. For said reason, the slow motion measurement arrangement is combined with a second, independent system, which allows for a fast motion measurement.

Operating principle of the fast motion measurement arrangement:

For the fast motion measurement arrangement, a small part of the eye fundus 6 is illuminated with a coherent IR laser illumination 12. The diameter of the coherently illuminated area in the eye fundus 6 lies approximately between 1° and 10° in the plane angle, whereby the radiation exposure of the eye fundus 6 is as low as possible, and it is therefore significantly smaller than the image field of the fundus camera detector 10. However, the illuminated area with a diameter between 1° and 10° is significantly larger than that of a typical confocal spot illumination. The light reflected from the eye fundus 6 interferes in the form of a speckle pattern, which is recorded into sectional images by a spatially resolving detector 15 with low resolution. Examples for the technical design of the detector are CCD, CMOS, or InGaAs cameras, whereby preferably only a small image section (region of interest or ROI) is read. The aperture of the detection optics 9B is designed in such a way that the size of the speckles, created through the coherent properties of the illumination source 12, is at least equal to the pixels of the detector 15.

Subsequently, from the sectional images taken in such a fashion, the relative shift to the respective preceding image or to a first sectional image is calculated via a cross-correlation after recording an additional overview image or alternatively estimated via an observation of the optical flow. An additional option for increasing the speed of the calculation of the cross-correlation is to not calculate all the points of the cross-correlation.

Only nine pixels (3×3) of the cross-correlation are calculated, i.e., the pixel of the expected shift between the two sectional images and its closest neighbors in each direction. This way, the exact shift (preferably with sub-pixel interpolation) is calculated and serves as an estimation of the shift to the next sectional image. In the subsequent sectional image, only the 9 pixels of the cross-correlation are calculated, which correspond to the expected shift between the two sectional images. With this type of evaluation, the period of computation can be decreased by a factor of 100 with a typical pixel array (with, e.g., 30×30 pixels). The only requirement to be met: The acceleration of the shift must not exceed a certain limit.

The size of the recorded sectional images and/or the sub-images of the sectional images used for the correlation is approximately 10×10 pixels to 100×100 pixels, so that only relatively few data are to be analyzed, resulting in a significantly faster analysis. As target specification, the fast motion measurement arrangement should preferably record an image, read, and analyze the shift data within 5 ms. Thereby, the analysis can be performed in a standard computer or preferably in special analysis electronics, such as a so-called smart pixel camera.

Due to the coherent illumination, structurally strong interference patterns, which can be registered significantly better, are imprinted on the relatively structureless fundus 6. A further advantage of the method is the possibility of the measurement of the movement of the eye fundus 6 even in an unideally focused condition of the detector 15 (of the detection optics 9B) due to the specific properties of the speckles.

Particularly preferred is the recording and analysis of the sectional images of the fast motion measurement arrangement with a commercially available laser mouse sensor. Such sensors were designed for the measurement of movements via a scattering background while utilizing specular reflections under the glancing angle, as disclosed, e.g., in U.S. Pat. Nos. 7,161,682 B2 and 5,786,804.

However, the principle of the analysis, usually hard-wired in the sensor, can be used for recording and analysis of the speckle-pattern sectional images with surprising cost-efficiency. However, no specular reflections are analyzed in the embodiment variation depicted herein since they occur essentially through a 3D surface curvature of a scattering surface while a volume scatterer layer (retina) with an approximate thickness of 0.5 mm is to be detected on the eye fundus 6. The same applies for alternative embodiments for the measurement on the sclera.

The detector 15 of the laser mouse sensor is positioned in the fundus camera 1 in a plane ZB (intermediate image plane), conjugated to the eye fundus. Thereby, as described in U.S. Pat. No. 7,161,682 B2, either all in the detection beam path positioned optics and beam-limiting surfaces are eliminated and/or the image, conjugated to the eye fundus, is positioned in the optimal focal point of the detection optics described therein. In both cases, the aperture of the optical detection system 9B is limited through a diaphragm and/or selection of an appropriate imaging scale in such a way that the occurring detection speckles are larger than the pixels of the detector 15.

A fundus camera 1 essentially corresponds to a biological microscope with the help of which the eye fundus can be depicted. Due to the specific geometry of the human eye, special technical configuration options are provided in a fundus camera 1 in order to be able to record as optimal an image of the eye fundus 6 as possible. One element of said specific optics is a ring illumination in the pupil 5 of the eye 2. Said illumination is selected in order to suppress a light reflection of the anterior of the cornea in the detection beam path. Thereto, an illumination ring 3, with, e.g., an outer diameter of 5.5 mm and an inner diameter of 3.5 mm, is projected as a virtual illumination source in the cornea plane of the human eye 2, and which illuminates the eye fundus 6 as evenly as possible at angles of field of approximately up to 22°. The radiation, which is emitted, e.g., from a circular fiber bundle 3, is imaged through optics 16 onto a circular mirror 13 which is also positioned in a plane conjugated to the eye pupil 5. The radiation backscattered from the eye fundus 6 passes through the hole in the ring mirror 13 and is imaged on the second detector 15.

Said second detector 15 is positioned in an intermediate image plane ZB, conjugated to the eye fundus 6. The thus described design corresponds to a standard fundus camera and represents in this embodiment the slow part of the combined motion measurement arrangement.

Figure 4:
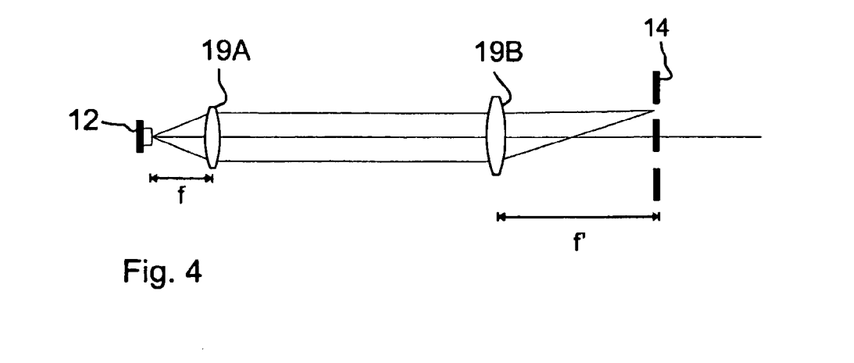
FIG. 4 is a schematic representation of an illumination beam path.

For the fast part, a coherent IR laser illumination 12 is collimated with optics 19A and subsequently focused through a second lens 19B on a ring aperture 14, which is positioned in a plane conjugated to the pupil plane, as is depicted in detail in FIG. 4. Then the coherent IR light is superimposed via a dichroic or half-mirror as beam combiner 20 with the illumination beam path of the first, incoherent IR light source 3 (FIG. 3). Subsequently, the IR light is directed through the optics 16, 4 of the fundus camera 1 onto the eye fundus 6 and illuminates a surface with a plane diameter between 1° and 10° (FIG. 3).

The light backscattered from the eye fundus 6 is split off from the fundus camera beam path through an additional dichroic or half-mirror and imaged on the second detector 15, which is conjugated to the eye fundus 6 (FIG. 3). Through the illumination of the eye fundus 6 with coherent light and the imaging of the backscattered light on the second detector 15, two types of speckles are formed, subjective detection speckles and objective illumination speckles. The subjective detection speckles are used to measure the movement of the eye fundus 6, while the objective illumination speckles represent a disturbance variable. In order to limit the interfering influence of the objective illumination speckles, the coherent illumination is focused preferably in a plane conjugated to the eye pupil (ring aperture 14). As a result, the illumination speckles in the fundus 6 are of a size which approximately corresponds to the beam diameter in the eye fundus 6 and therefore pose no problem for the further course of the method. For the second light source 12, semiconductor laser sources are preferably utilized; however, all other types of coherent light sources with coherence lengths of approximately more than 0.5 mm (the coherence length should preferably correspond to at least twice the thickness of the retina in order to achieve a satisfactory speckle pattern contrast on the detector 15) and good spatial coherence can also be used for the method.

A further specific characteristic of fundus camera illumination optics is the introduction of antireflexion points (apertures) in the illumination beam path, which are to prevent reflections at the front objective of the fundus camera into the detection beam path. If said antireflexion points are not optimally adjusted, or if some of the optical elements of the illumination beam path are slightly scattering due to dust particles, a typical circular reflection can be detected in the detector image of the fundus camera, which also occurs in the laser mouse beam path, and which can lead to problems during the motion measurement. For such reason, the use of a non-reflective front objective is particularly preferred. A second preferred variation for the use of standard objectives in the fundus camera is a slightly off-axis illumination and an adjusted off-axis detection.

Figure 5:
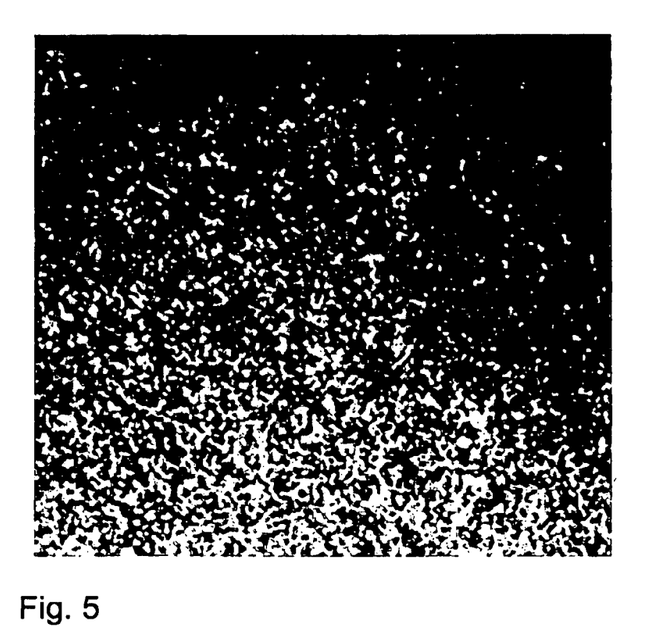
FIG. 5 is a sectional image with a speckle pattern taken from a demonstration eye.

FIG. 5 shows a speckle pattern imaged with coherent illumination of an eye fundus 6.

In cases which require great accuracy (e.g., femtosecond Lasik, fs-Lasik), a contact glass is inserted in order to define the position of the eye during refractive surgical therapy of the cornea. In this case, a movement of the eye is theoretically impossible. However, shifts of the eye parallel to the contact glass can occur with stronger forces between eye and contact glass. In this case, said shifts have to be measured very quickly in order to tracking-adjust or deactivate the therapy laser. The arrangement, according to the invention, solves exactly such measuring task with only one detector with particular ease and cost-efficiency.

Figure 6:
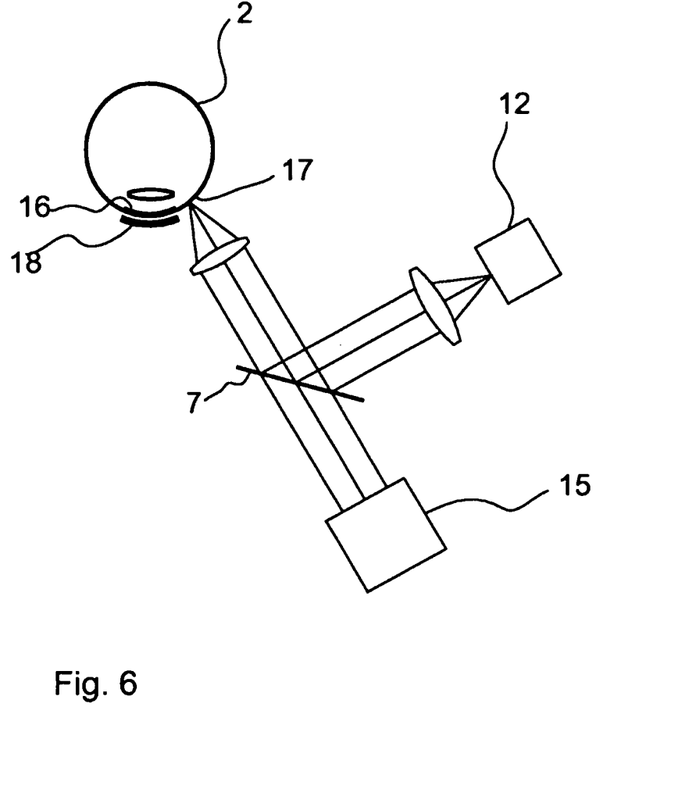
FIG. 6 is a schematic representation of an eye motion tracking arrangement with only one detector.

FIG. 6 shows a schematic depiction of the basic set-up of the motion measurement arrangement. The beam path of the Lasik laser (not depicted) for the treatment of the cornea 16 remains unchanged. For the realization of the motion measurement arrangement, a highly coherent laser beam of the light source 12 is focused on the sclera 17 of the eye 2 next to the contact glass 18 or at its edge through the contact glass 18.

The light backscattered from the sclera 17 is imaged greatly magnified through detection optics (not depicted) onto a single, spatially resolving camera sensor 15. Since only a very small image field has to be imaged onto the camera sensor 15, the requirements with regard to quality of the optics are relatively low. The resolution of the optical system is chosen in such a way that it corresponds with the achievable measurement accuracy of the motion measurement arrangement. In the case of fs-Lasik, the resolution should lie between 1 µm and 3 µm. Thereto, an objective with a relatively high numerical aperture is required. For the analysis of the data, an image field with a diameter of approximately ten speckles suffices. With a resolution of 1 µm, this corresponds to an image field of approximately 10 µm. Such small image fields can be realized with relatively little effort through the illumination with strictly monochromatic laser light. During the motion measurement, the camera sensor 15 records sectional images of the sclera 17 with a very high image refresh rate and calculates the cross-correlation of immediately consecutive images. The position of the maximum of the cross-correlation function indicates the relative shift of the scattering sclera 17 between the sectional recordings. The camera sensor 15 must be dimensioned in its image field in such a way that the shift between two sectional images is never greater than the image field of the camera sensor 15. With this arrangement, attention must be paid to the fact that only the relative shift between the images can be calculated. This means that the absolute position determination of the eye becomes less certain with the number of sectional images due to the propagation of measuring errors.

In order to be able to measure movements and/or positions of the eye quasi-absolutely, the third sectional image to be measured, after the beginning of the measurement, is cross-correlated not against the second sectional image but once again against the first sectional image in order to determine the shift to the first sectional image. This is possible as long as the relative shifts of the two images are smaller than the image field of the sensor. In order to develop a global measure, the various sectional images are assembled mosaic-like to a full-surface overview image by means of the correlation algorithms. Then a further image is correlated exclusively with one part of said global overview image. With said analysis method, the positional inaccuracy no longer increases with the number of images but solely with the relative distance to the center of the first sectional image.

With the shift sensor thus described, a measurement accuracy between 1 µm and 3 µm can be achieved at an effective image refresh rate between 1 kHz and 10 kHz correspondingly.

Legend
1 Fundus camera
2 Eye
3 First light source
4 Front objective
5 Pupil
6 Fundus
7 Beam splitter
8 Aperture
9 Detection optics
10 First detector
11 Control unit
12 Second light source
13 Ring mirror
14 Ring aperture
15 Second detector
16 Cornea
17 Sclera
18 Cover glass
19 Illumination optics
20 Beam combiner
A Imaging beam path
B Illumination beam path
ZB Intermediate image plane
f, f' Focal lengths

The invention claimed is:

1. An arrangement for measurement of a movement of an eye, comprising:
a first two-dimensional spatially resolving detector that repeatedly images a potential motion field of the eye in overview images at a first image refresh rate;
a second two-dimensional spatially resolving detector that repeatedly images a respective segment of the eye in sectional images at a second image refresh rate, which is higher than the first image refresh rate;
a data processor that determines a first intermediate shift between two overview images, and a second intermediate shift between two sectional images, and that determines a movement of the eye though interlinking of said shifts;
a first light source that illuminates the potential motion field of the eye with incoherent light;
a second light source that illuminates the respective segment of the eye with coherent light such that a speckle pattern occurs in the respective segment through interfering, coherent light, scattered at the eye; and
wherein the second detector is structured to record at least one part of the speckle pattern in the respective sectional image.

2. The arrangement, according to claim 1, wherein the second detector comprises optics that image a magnified image of the speckle pattern onto the second detector such that individual speckles of the speckle pattern in the image exhibit a size which approximately corresponds to or is larger than a size of image elements of the second detector.

3. The arrangement, according to claim 1, wherein the arrangement is configured for the measurement of a movement of a fundus of the eye;
wherein the first light source illuminates the eye fundus with infrared light;
wherein the first detector records at least one part of the eye fundus as the potential motion field of the eye; and
wherein the second light source illuminates a respective segment of the eye fundus with infrared light.

4. The arrangement, according to claim 1, wherein the second light source is structured to emit light in an illumination angle between 1° and 10°.

5. The arrangement, according to claim 1, wherein the second light source projects an essentially circular-shaped image in the plane of the eye pupil.

6. The arrangement, according to claim 1, wherein the second light source is structured to focus the coherent light in a plane, which is conjugated to a pupil of the eye.

7. The arrangement, according claim 1, wherein a median angle of incidence of the coherent light of the second light source onto the eye essentially corresponds to an observation direction of the second detector.

8. The arrangement, according to claim 1, wherein the second detector comprises a detector of a laser mouse.

9. The arrangement, according to claim 1, wherein the second detector is positioned in a plane, which is optically conjugated to the respective segment.

10. The arrangement, according to claim 1, wherein the data processor determines the second shift through comparison of at least one respective part of the image content of the respective two images at coherent illumination.

11. The arrangement, according to claim 10, wherein the data processor determines the second shift through comparison of at least one respective part of the recorded speckle pattern.

12. A method of measurement of a movement of an eye, comprising:
repeatedly recording at least one potential motion field of the eye in overview images with a first image refresh rate with a first two-dimensional spatially resolving detector;
repeatedly recording sectional images with a second image refresh rate, which is higher than the first image refresh rate, with a second two-dimensional spatially resolving detector;
determining a first intermediate shift by use of two overview images;
determining a second intermediate shift by use of two sectional images; and
determining a movement of the eye through interlinking of the two shifts;
illuminating the potential motion field of the eye with incoherent light from a first light;
illuminating the respective segment of the eye with coherent light such that a speckle pattern occurs in the respective segment through interfering, coherent light, scattered at the eye from a second light source; and
recording at least one part of the speckle pattern in the respective sectional image via the second two-dimensional spatially resolving detector.

13. A non-transitory computer readable data medium, comprising instructions to a computer to:
repeatedly record at least one potential motion field of the eye in overview images with a first image refresh rate with a first two-dimensional spatially resolving detector;
repeatedly map sectional images with a second image refresh rate, which is higher than the first image refresh rate, with a second two-dimensional spatially resolving detector;
determine a first intermediate shift by use of two overview images;
determine a second intermediate shift by use of two sectional images; and determine a movement of the eye through interlinking of the two shifts;

illuminating the potential motion field of the eye with incoherent light from a first light;

illuminating the respective segment of the eye with coherent light such that a speckle pattern occurs in the respective segment through interfering, coherent light, scattered at the eye from a second light source; and recording at least one part of the speckle pattern in the respective sectional image via the second two-dimensional spatially resolving detector.

* * * * *